(12) United States Patent
Wolfschaffner

(10) Patent No.: US 7,690,268 B2
(45) Date of Patent: Apr. 6, 2010

(54) METHOD AND DEVICE FOR THE CONTINUOUS GRAVIMETRIC METERING OF FLOWING MATERIALS FOR BURNER SYSTEMS

(75) Inventor: Hubert Wolfschaffner, Dasing (DE)

(73) Assignee: Pfister GmbH (DE)

( * ) Notice: Subject to any disclaimer, the term of this patent is extended or adjusted under 35 U.S.C. 154(b) by 692 days.

(21) Appl. No.: 10/563,454

(22) PCT Filed: Jul. 4, 2004

(86) PCT No.: PCT/EP2004/007289
§ 371 (c)(1),
(2), (4) Date: Jan. 18, 2007

(87) PCT Pub. No.: WO2005/003696
PCT Pub. Date: Jan. 13, 2005

(65) Prior Publication Data
US 2009/0133507 A1 May 28, 2009

(30) Foreign Application Priority Data
Jul. 4, 2003 (DE) .................... 103 30 376

(51) Int. Cl.
*G01F 1/78* (2006.01)
(52) U.S. Cl. ................................. 73/861.351
(58) Field of Classification Search .......... 73/861.351, 73/861; 239/7, 677; 177/114; 209/524, 209/580, 585; 432/194
See application file for complete search history.

(56) References Cited
U.S. PATENT DOCUMENTS
3,412,699 A 11/1968 Culp

| 4,277,022 | A | * | 7/1981 | Holdsworth et al. | 239/7 |
|---|---|---|---|---|---|
| 4,915,306 | A | | 4/1990 | Peet | |
| 5,121,638 | A | * | 6/1992 | Gmur | 73/861 |
| 5,794,788 | A | * | 8/1998 | Massen | 209/524 |
| 6,884,064 | B1 | * | 4/2005 | Cusick et al. | 432/194 |
| 2002/0078868 | A1 | | 6/2002 | Alpern et al. | |

FOREIGN PATENT DOCUMENTS
DE 44 43 053 A1 6/1996
WO WO 01/61285 A1 8/2001

* cited by examiner

*Primary Examiner*—Jewel Thompson
(74) *Attorney, Agent, or Firm*—Knobbe Martens Olson & Bear LLP

(57) ABSTRACT

A method for the continuous gravimetric metering of flowing materials for burner systems, in which the instantaneous mass flow is determined and metering occurs by means of a metering unit can be achieved by means of determination of the type of flowing material. The instantaneous heat output for the flowing material is determined from the type of flowing material and the heat capacity thereof and the mass flow determination. The output from the metering device is regulated to match the set feed rate, depending on the instantaneous heat output. In addition, a device for the continuous gravimetric metering of flowing materials for burner systems comprises a metering unit by means of which the flowing material can be metered. Also provided is a material recognition system for determining the type of the flowing material, an arithmetic unit for determining the instantaneous heat output of the flowing material and a metering controller by means of which the output from the metering unit is regulated to match the set feed rate, depending on the instantaneous heat output.

13 Claims, 3 Drawing Sheets

METHOD AND DEVICE FOR THE CONTINUOUS GRAVIMETRIC METERING OF FLOWING MATERIALS FOR BURNER SYSTEMS

BACKGROUND

Numerous apparatuses and methods for the continuous gravimetric metering of flowing materials for burner systems are known from the state of the art. Flowing materials are understood as being all materials which can be used for fuelling burner systems. Coal dust and waste of all kinds, and in particular plastic waste, are hereby mentioned as examples. The flowing materials can be present both in the form of particles as well as in coarse form. The plastic waste can be shredded, e.g. shreds of waste tires or carpets, or it can be used in an unchanged way, e.g. in the form of plastic containers and packaging. The flowing materials are usually stored in a silo or bunker and supplied with the help of metering and transport apparatuses to the burner system, e.g. a rotary kiln in the production of cement.

Such systems for continuous gravimetric conveyance and/or mixing of pourable material are known for example from DE 40 23 948 A1, with a rotary metering weigher according to DE 32 17 406 A1 or EP-A-0 198 956 being used, because such a metering apparatus can be used in an enclosed pneumatic conveying path to continuously determine the flow of pourable material situated therein and the throughput of pourable material can be influenced by varying the supplied quantity of air per unit of time or by changing the speed. A computer-controlled central metering control system is used for the respective control of the desired mixture ratio or the desired conveyed quantity per unit of time (conveying rate), as is described for example in DE 32 17 406. The weighing signal of the bunker weighing cells is used as an input signal and especially the speed of the metering rotor is controlled for the supply of the pourable material.

Such an apparatus is further known from DE 44 43 053. The apparatus described therein for the continuous gravimetric metering and determination of mass flow of flowing materials comprises a flow meter, especially a Coriolis metering wheel for determining the instantaneous mass flow, and a metering device connected downstream of the flow meter. The flow meter is connected with the metering device via a metering control unit and the delivery of the metering device can be controlled in a time-shifted manner on the flow meter depending on the deviations in the mass flow.

It is becoming increasingly more important to govern the supply in such a way that the combustion process can occur in an optimal manner where the supply of flowing materials to burner systems is concerned, especially in cases where different types of flowing materials are to be supplied, as a result of environmental and economical considerations. This means that the supply of flowing materials as a fuel and the supply of air must be controlled in such a way that the combustion processes can run optimally and the desired temperature can be kept constant at the same time. The problem arises in connection with different fuels that the calorific value of the individual goods or the flowing materials cannot be determined in their entirety until the present day. For this reason, only a part of the usually employed fuels, e.g. coal dust for rotary kilns for the production of cement, are currently partly replaced by alternative fuels such as plastic waste. It is also often tried to add merely one single type of plastic material, because the calorific values of the individual types of plastic are differently high. Plastic material of a "pure assortment" has a calorific value which lies in the magnitude of crude oil, whereas fractions of mixed plastic materials as are obtained especially in waste management have a calorific value which is close to that of wood or coal.

SUMMARY

It is the object of the present invention to provide a method and an apparatus for continuous gravimetric metering of flowing materials for burner systems with which a metering of the flowing materials can be performed depending on the condition and the calorific value of the respective goods.

The instantaneous mass flow is determined in the method in accordance with the invention with the help of a flow meter or in combination with a metering device, e.g. a belt weigher or a Coriolis metering wheel. The mass of the continuously flowing materials is thus continuously determined. In addition to the determination of the mass, there is also a determination as to which type of flowing material flows past. It is thus determined whether coal dust, plastic materials, waste carpets, waste tires, wood or other combustible goods are provided for supply to the furnace. The type of plastic materials is further determined, e.g. whether polyethyleneterephthalate (PET), polypropylene (PP), polyvinyl chloride (PVC) or plastic-coated materials are contained. In particular, the respective type of recycling plastics are to be determined. Since the calorific value is known for each of the known flowing materials, the instantaneous calorific value of the flowing materials is determined from the data of mass flow determination and from the data of the determination of the type of flowing material and its known individual calorific value. The instantaneous calorific value is designated as such calorific value of the flowing materials which are supplied momentarily (at the time of determining the mass and type) to the furnace. The delivery of the metering device is then regulated in adjustment to the setpoint conveying rate depending on the instantaneous calorific value. Such a regulation occurs for example in such a way that the furnace is supplied with more or less fuel or that a regulation of the air supply occurs. As a result of the method in accordance with the invention and the respective apparatus in accordance with the invention with which the method in accordance with the invention is performed it is advantageously ensured that the calorific value of each individual fraction of flowing materials will be known prior to the supply to the furnace and a precise regulation of the metering can occur. It is no longer necessary to make estimates concerning the possible calorific value. Instead, there are precise data for this purpose. The combustion process can thus be optimized and the ecological and economic aspects are considered optimally.

BRIEF DESCRIPTION OF THE DRAWING

The invention is now explained in closer detail by reference to the enclosed drawings, wherein.

DETAILED DESCRIPTION

Figure 1:
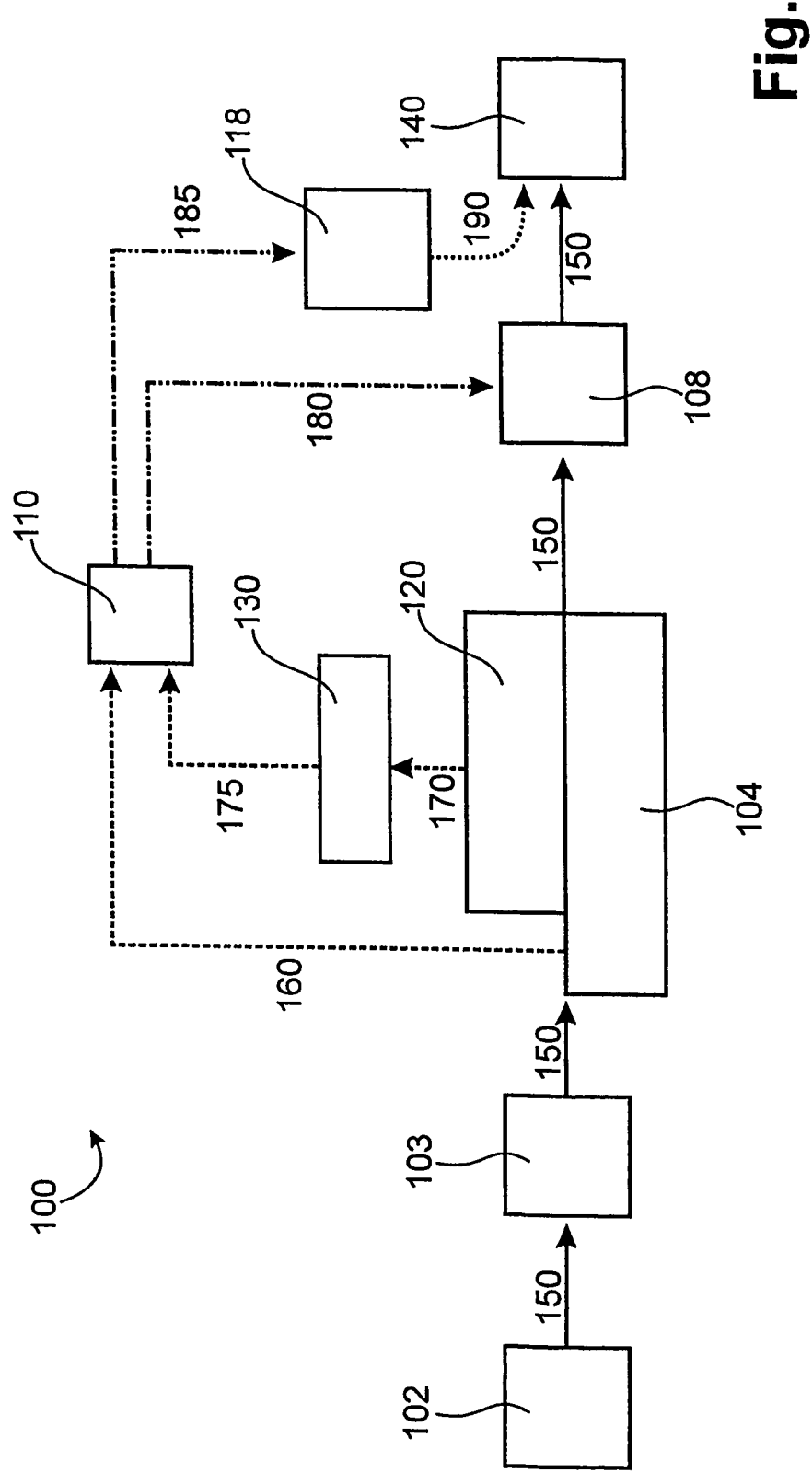
FIG. 1 shows a block diagram of an apparatus in accordance with the invention.
Figure 3:
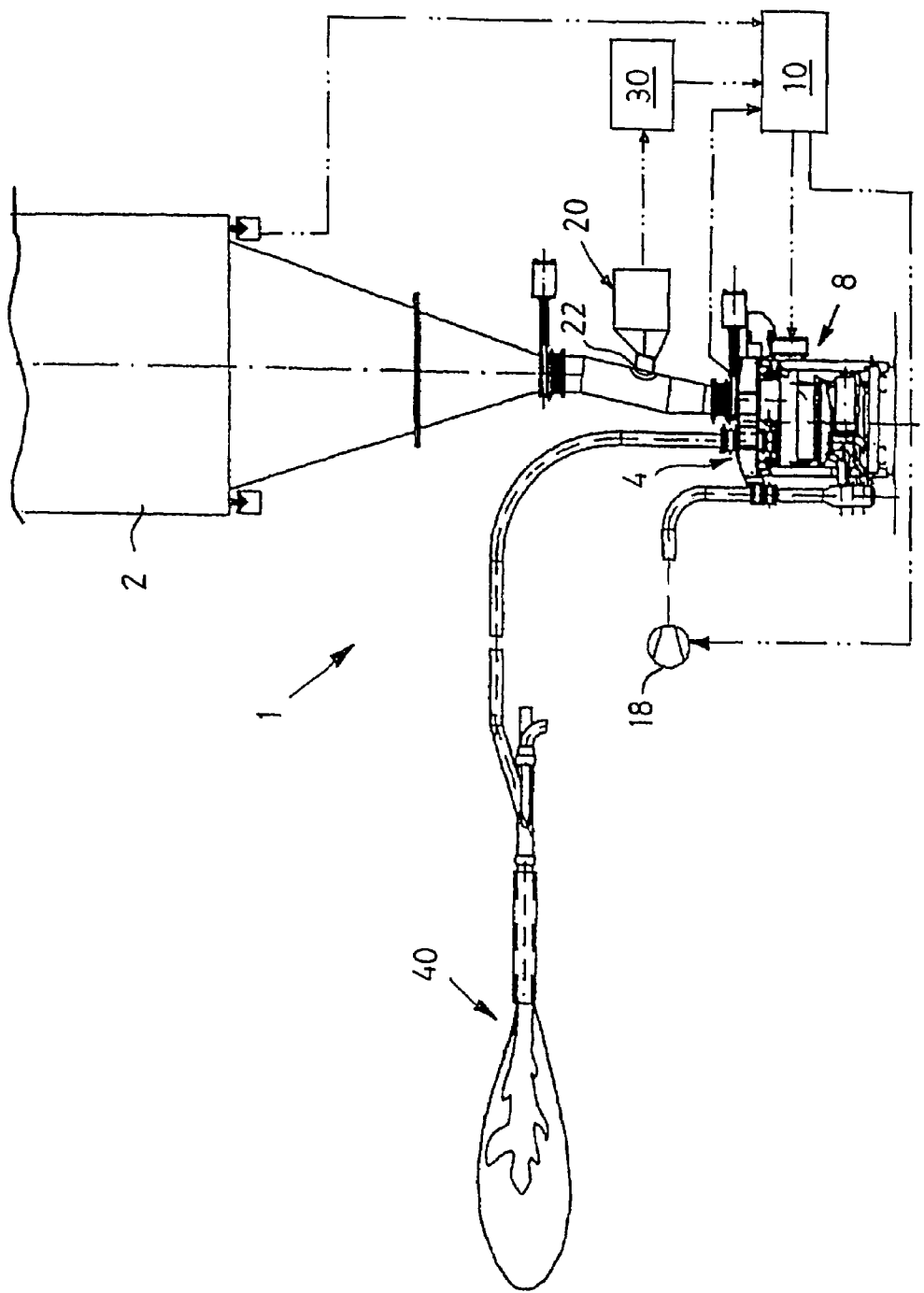
FIG. 3 shows a further preferred embodiment in the form of a rotary metering weigher.

FIG. 1 shows a schematic view of an embodiment of the invention. The illustration shows a schematic configuration of an apparatus 100 and the respective signal and material flows. Flowing materials are supplied both to the flow meter 104 and to the material recognition system 120 from a silo 102 with the help of a draw-off apparatus 103. The flow of the fuels is shown in FIG. 1 with an unbroken arrow 150. After passing through the flow meter 104, these materials flow further via a meter device 108 to the burner system 140. All known apparatuses can be used as draw-off apparatus 103, e.g. cellular wheel sluices or metering worms. A large number of known flow meters can also be used as flow meters, with a belt weigher preferably being used as a flow meter 104 in the embodiment according to FIG. 1. Different apparatuses can also be used as the metering device 108, e.g. cellular wheel sluices or metering worms or, as shown in FIG. 3, a rotary metering weigher as a combination or module of the two. A rotary kiln is preferably used as a burner system 140, as is used in the production of cement for example. It is also possible to use other burner systems, e.g. burner systems in power plants. The flowing fuel materials not only flow through the flow meter 104 but also through the material recognition system 120. The material recognition system is arranged in or above the flow meter 104 in the embodiment of FIG. 1. The material recognition system 120 can also be arranged directly before the metering device or directly after the flow meter 104.

The material recognition system 120 comprises a contactless material sensor, especially a microwave sensor, X-ray sensor or NIR spectroscopic sensor. The material recognition system 120 further comprises a radiation source with which the flowing material can be irradiated with a radiation to which the material sensor is sensitive. An NIR spectroscopic sensor is preferably used. Every flowing material is thus recognized with the help of the material recognition system 120. The data determined in the material recognition system is forwarded to the computer unit 130 (arrow 170). An evaluation of the data occurs there, with the type of the determined flowing materials being linked with the respective calorific value. The data linked in the computer unit is then sent to the metering control unit 110 (arrow 175). The metering control unit 110 also receives the data on the determination of the mass flow (arrow 160) which is determined by the flow meter 104.

As shown in FIG. 1, the parameters received by the metering control unit 110 are shown with broken lines. The metering control unit 110 evaluates the received data and determines the instantaneous calorific value of the flowing materials. The delivery of the metering device 108 is regulated in adjustment to the setpoint conveying rate depending on the instantaneous calorific value. This is indicated by the dot-dash arrow 180. A further possibility for regulation is regulating the air supply to the burner system 140, which is carried out with the help of the control unit of a blower 118 (arrow 185). Any signals originating from the metering control unit are shown with a dot-dash line. The blower 118 regulates the supply of air to the burner system 140, illustrated by the arrow 190. The combustion of the flowing materials in the burner system 140 can occur both via a regulation of the metering device 108 so that more or less flowing fuels are conveyed, as well as via a regulation of the blower 118, as a result of which the supply of air is increased or reduced.

Figure 2:
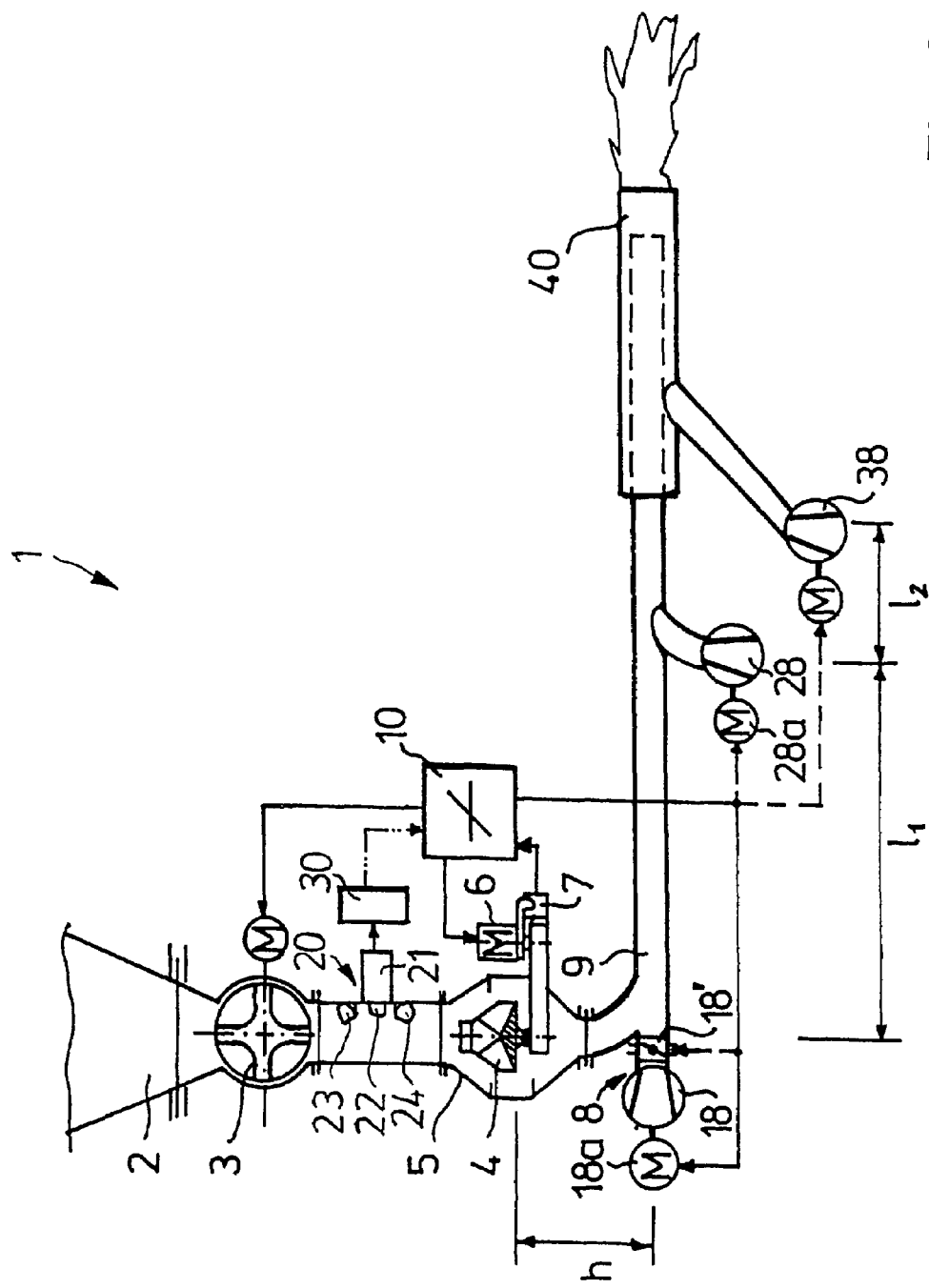
FIG. 2 shows a schematic view of an embodiment of the invention.

FIG. 2 shows an apparatus 1 for the continuous gravimetric metering and determination of mass flow, with the conveying material to be metered according to an adjustable setpoint conveying rate, especially a pourable flowing material, is supplied from a bunker or silo 2 by means of a draw-off apparatus 3 configured here in the form of a cellular wheel sluice. The conveyed material reaches a flow meter 4 which is arranged within a housing 5 and thus defines a measuring section. The flow meter 4 is configured here as a Coriolis metering wheel, as is described in closer detail in DE 41 34 319 A1. This Coriolois metering wheel is held in this case on a drive housing projecting laterally from the housing 5 and is driven by an electromotor 6 which rests on a load cell 7 by way of a jib in a limited pivoting movable way. The required torque of the metering wheel rotating at an approximately constant speed changes here according to the occurring Coriolis force, with the change of the drive torque and thus the reaction moment on the laterally arranged load cell 7 being directly proportional to the mass of the material flow which flows through.

The power consumption of the drive motor 6 can also be used for detecting the change in torque and thus the determination of the mass flow. The flow meter 4 according to the Coriolis metering principle comes with the advantage of a very high measuring precision. It is also possible to use other flow meters such as baffle-plate continuous-flow weighing machines or inductive or capacitive flow meters.

A pneumatic conveyor 18 is provided in this case as a metering device 8 for metering and further conveying the flowing materials. It opens into the blow-out line 9. The transducer of the flow meter 4, which in this case is the load cell 7, is connected with the metering control unit 10, which thus determines the instantaneous mass flow and places the same in relationship to the setpoint conveying rate, and thus directly triggers the motor 18a of the metering device 8 in order to vary the speed of the pneumatic conveyor 18 and to thus keep the set conveying rate constant. If the flow meter 4 thus measures a negative deviation of the mass flow, the speed of the pneumatic conveyor 18 is increased by the respective value in order to maintain the conveying rate. A relevant aspect is also that as a result of the arrangement of the dosing device 8 at a certain distance from the flow meter 4 or the burner system 40, geometrically predetermined conditions are present, so that metering control unit 10 is capable of calculating precisely the time at which the disturbance occurred in the blow-out line 9. This can also be placed in relationship with the instantaneous calorific value as determined by the material recognition system 120. As a result, the metering control unit 10 can give the respective command at this time or shortly before by taking into account the inertial behavior of the metering device 8 to increase the speed by 0.2% for example. A kind of anticipatory regulation of the actual conveying rate is thus enabled by this apparatus 1.

In order to substantially maintain the constancy of the mass flow supplied to the flow meter 4, the draw-off apparatus 3 can be controlled or regulated in an advantageous embodiment according to the measurement results of the flow meter 4. In an especially simple embodiment it is sufficient to branch off a drive from the drive motor 18a and an associated transmission of the metering device 8 in order to achieve a synchronous regulation of draw-off apparatus 3 and dosing device 8. It is understood that certainly separate motors could be provided which are triggered by the meter control unit 10 in an electronically coupled way.

In accordance with the invention, the apparatus 1 comprises a material recognition system 20 (similar to the one in FIG. 4 with reference numeral 120), which is arranged in this case before the flow meter 4 however. The material recognition system 20 comprises an NIR spectrometer 21 in the embodiment of FIG. 2. A material sensor 22, which more precisely is an NIR spectroscopic sensor, receives the light absorption of the flowing materials that flow past. The flowing materials are illuminated homogeneously with NIR light, for which the radiation sources 23 and 24 are provided. A halogen lamp can be used as such a source of radiation for example. The material sensor 22 is contactless and collects the transmitted and reflected light irrespective of the distance to the flowing materials and guides the same forward via suitable optical waveguides to the spectrometer 21. Since the different types of flowing materials each have a characteristic light absorption, they can thus be recognized. The near infrared range extends in the spectral range of 850 to 2200 nm. In this wavelength range, the O—H—, N—H— or C—H-molecule oscillations for example show clear absorption bands. By evaluating the extinction of the individual bands it is thus possible to make precise statements on the composition even of complex mixtures. This can occur directly on site during the supply of the flowing materials to the burner system 40 and supplies the results in real time. The data is forwarded by the spectrometer 21 to the computer unit 30 where it is compared with the data of fuels as known from calibration methods or known sources and is associated with the respectively know calorific values. This data is then supplied to the metering control unit 10 which regulates the conveying rate in adjustment to the setpoint conveying rate with the help of the data obtained in the flow meter 4 by taking into account the instantaneous calorific value of the fuel supplied to the system. A regulation of the metering device and also the draw-off device can thus occur.

A further possibility for regulation is that a metering flap 18' is provided on the pneumatic conveyor 18 which changes the air flow and thus controls the output from the housing 5 depending on instantaneous mass flow and calorific value as determined by the flow meter 4. Depending on a positive or negative deviation, the air injection by the pneumatic conveyor 18 can be varied as a consequence of the speed regulation of the drive motor 18a and/or the opening or closing of the metering flap 18' in order to maintain the setpoint conveying rate.

A further possibility is that an additional blower 28 is connected to the blow-out line 9, with the drive motor 28a of the additional blower 28 being connected to the metering control unit 10, as is shown originating from a data linkage point in unbroken lines. Instead of changing the secondary air quantity and/or air speed, it is possible to readjust a primary air blower 38 as a further alternative. Fixed distances, which are h+l1+l2 in this case, and thus time differences between the flow meter 4 and the orifice into the burner system 40 are predetermined. The change of the primary air supply is especially relevant in this case in burner systems 40 for maintaining the air/fuel ratio. As a result, the three illustrated blowers 18, 28 and 38 are preferably coupled with each other in a controller integrated in the metering control unit 10 for example, so that in the case of an increase in the air quantity in the blower 18 a respective reduction of the supplied air quantity is made in the blower 38 in order to maintain not only the supplied fuel quantity but also the preferably stoichiometric air/fuel ratio according to the setpoint values.

FIG. 3 shows a preferred embodiment of the apparatus (with the same reference numerals for respective components), namely with a rotary metering weigher of the configuration as mentioned above. This configuration of the rotary metering weigher as a metering device 8 simultaneously integrates the flow meter 4 as a result of its configuration, as is indicated by the double arrow designation. This leads to an especially compact configuration of the apparatus in a module, so that the individual components as shown in FIGS. 1 and 2 are combined in a practical way in one metering device. The material recognition system 20 which is relevant here can be arranged shortly before the material inlet from the bunker 2. It can also be integrated in the housing of the rotary metering weigher 4 and 8. The same applies for similar metering devices of the applicant, e.g. metering chain weighers.

The invention claimed is:

1. A method for the continuous gravimetric metering of flowing materials for burner systems, with the instantaneous mass flow being determined and the metering occurring with a metering device, wherein
the type of each flowing material is determined, the known individual calorific value from the type of each flowing material is determined and the instantaneous calorific value of the flowing materials is determined from the determination of the mass flow and the output from the metering device is regulated in adjustment to the setpoint conveying rate depending on the instantaneous calorific value.

2. A method according to claim 1, wherein the determination of type of flowing material is carried out by way of NIR spectroscopy.

3. A method according to claim 1, wherein the flowing materials are plastic materials.

4. A method according to claim 1, wherein the output of the metering device is regulated by taking into account the distance between metering device and burner system.

5. A method according to claim 1, wherein the output of the metering device is controlled or regulated by changing the speed of the metering device.

6. A method according to claim 1, wherein the output of the metering device is regulated in the case of pneumatic conveyance by changing the air quantity and/or air speed.

7. An apparatus for the continuous gravimetric metering of flowing materials for burner systems, with the instantaneous mass flow being determined and with the flowing materials being metered by means of a metering device, wherein
there are provided a material recognition system for determining any kind of flowing material, a computer unit configured to receive information from the material recognition system and to determine the instantaneous calorific value of the flowing materials, and a metering control unit configured to adjust the output of the metering device to the set-point conveying rate based on the instantaneous calorific value.

8. An apparatus according to claim 7, wherein the material recognition system comprises a contactless material sensor and a radiation source with which the flowing material can be irradiated with a radiation to which the material sensor is sensitive.

9. An apparatus according to claim 8, wherein the material sensor is an NIR spectroscopic sensor and the radiation source emits light in the near-infrared range, especially that the radiation source is a halogen lamp.

10. An apparatus according to claim 7, wherein the material recognition system is arranged directly before the metering device.

11. An apparatus according to claim 7, wherein the flowing materials are plastic materials.

12. An apparatus according to claim 7, wherein the burner system is a rotary kiln for cement production.

13. An apparatus according to claim 7, wherein the metering device and the flow meter form a unit, especially a rotary metering weigher.

* * * * *